(12) United States Patent
Lee (10) Patent No.: US 6,278,112 B1
(45) Date of Patent: Aug. 21, 2001

(54) METHOD OF SETTING A BASE ENERGY LEVEL FOR AN AUGER ELECTRON SPECTROSCOPY ANALYSIS OF A TITANIUM NITRIDE FILM, AND METHOD OF ANALYZING THE TITANIUM NITRIDE FILM

(75) Inventor: Sang-eun Lee, Kyungki-do (KR)

(73) Assignee: Samsung Electronics Co., Ltd., Suwon (KR)

(*) Notice: Subject to any disclaimer, the term of this patent is extended or adjusted under 35 U.S.C. 154(b) by 0 days.

(21) Appl. No.: 09/221,829

(22) Filed: Dec. 28, 1998

(30) Foreign Application Priority Data

Dec. 29, 1997 (KR) .................................................. 97-76792

(51) Int. Cl.$^7$ ............................ H01J 40/00; H01J 47/00; G01N 23/00
(52) U.S. Cl. ............................................ 250/305; 250/307
(58) Field of Search .................................. 250/305, 307

(56) References Cited

U.S. PATENT DOCUMENTS 5,523,626 * 6/1996 Hayashi et al. ...................... 257/763
5,834,846 * 11/1998 Shinriki et al. ...................... 257/754
5,889,282 * 3/1999 Yang et al. ............................. 250/305
6,001,729 * 12/1999 Shinriki et al. ....................... 438/625

OTHER PUBLICATIONS

S. Hofman, "Characterization of nitride coatings by Auger electron spectroscopy and x-ray photoelectron spectroscopy," 1986 American Vacuum Society, J. Vac. Sci. Technol. A 4(6), Nov./Dec. 1986, pp. 2789–2796.

M.F.C. Willemsen et al., "In situ investigation of TiN formation on top of TiSi2," 1988 American Vacuum Society, J. Vac. Sci. Technol. B 6(1), Jan./Feb. 188, pp. 53–61.

* cited by examiner

Primary Examiner—Bruce C. Anderson
(74) Attorney, Agent, or Firm—Jones Volentine, PLLC (57) ABSTRACT

A quantitative and qualitative analysis of a nitrogen (N) kinetic energy peak in a spectrum of a titanium nitride (TiN) film using Auger Electron Spectroscopy (AES). The N kinetic energy peak analysis is used to set the base energy level of the AES, and is achieved by selecting a kinetic energy of an N peak which does not overlap with the Ti kinetic energy peak.

13 Claims, 7 Drawing Sheets

METHOD OF SETTING A BASE ENERGY LEVEL FOR AN AUGER ELECTRON SPECTROSCOPY ANALYSIS OF A TITANIUM NITRIDE FILM, AND METHOD OF ANALYZING THE TITANIUM NITRIDE FILM

BACKGROUND OF THE INVENTION

1. Field of the Invention

The present invention relates to a method of setting the base energy level for an Auger Electron Spectroscopy (AES) analysis of a Titanium Nitride (TiN) film, and a method of analyzing a TiN film, or a semiconductor device having a TiN film thereon. More particularly, the present invention employs AES to conduct a quantitative and qualitative analysis for the nitrogen (N) contained in the TiN films of the semiconductor devices.

2. Description of the Related Art

Metal film or metallic nitride films are often used in the semiconductor device fabrication process. In order to establish proper processing parameters, it is necessary to carry out a precise quantitative and qualitative analysis of the nitrogen and metal in the metallic nitride films.

However, the nitrogen analysis can not easily be performed prior to or after the process. Moreover, the analysis of the nitrogen content in the TiN film is further complicated by the fact that the titanium (Ti) peak and the main nitrogen (N) peak overlap, making a precise qualitative and quantitative analysis more difficult.

Generally, a conventional Scanning Electron Microscope (SEM) may be used to analyze the wafer prior to the fabrication of the semiconductor devices. Also, a Transmission Electron Microscope (TEM) may be used to analyze the structure of metallic samples, for example, the crystal structure of the samples, by scanning an accelerated electron beam toward the sample and analyzing the diffraction pattern. Moreover, an Auger analysis may be performed in which the secondary electrons emitted from the surface of the sample surface are examined. Such methods are well-known to those of ordinary skill in the art and are commercially available.

The Auger analysis, or Auger Electron Spectroscopy (AES), uses a method where excited atoms having high energy levels are brought to low energy levels by releasing electrons. While analyzing a certain portion of a wafer, if electrons having a certain energy are scanned on the sample, excited atoms release secondary electrons called Auger electrons as well as X-rays. By detecting the velocity or the distribution of the Auger electrons, the surface state of the sample can be examined, and the presence of a certain atom and its relative amount can be detected by measuring the energy of the Auger electrons.

Figure 1:
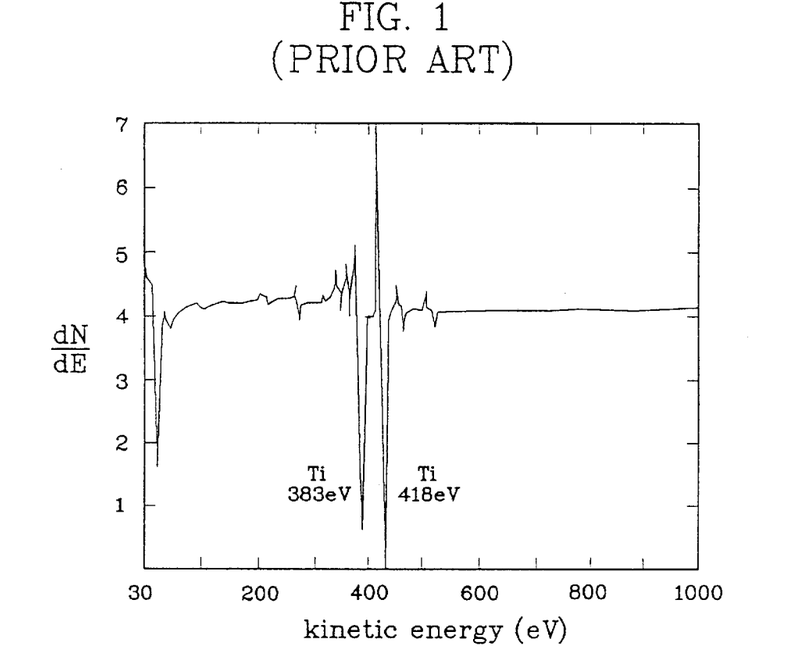
FIG. 1 shows a spectrum display of a standard Ti material obtained by conventional Auger Electron Spectroscopy (AES)
Figure 2:
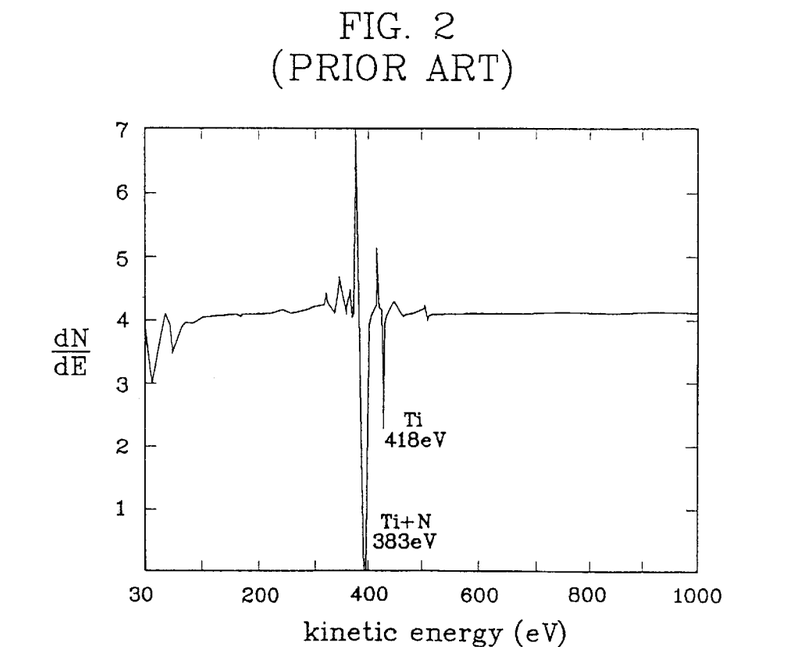
FIG. 2 shows a spectrum display of a standard TiN (Ti+N) material obtained by conventional AES.

However, as described above for TiN films, the analysis of the nitrogen in the TiN film is complicated since the titanium (Ti) Auger peak and the main nitrogen (N) Auger peak overlap, making a precise qualitative and quantitative analysis difficult. See, S. Hofmann, "Characterization of nitride coatings by Auger electron spectroscopy and x-ray photoelectron spectroscopy", *J. Vac. Sci. Technol. A* 4(6), November/December 1986, pp. 2789–96; and M. Willemsen et al., "In situ investigation of TiN formation on top of $TiSi_2$", *J. Vac. Sci. Technol. B* 6(1), January/February 1988, pp. 53–61. As described in the references, the Ti Auger peak of a standard Ti material (FIG. 1) and the Ti+N Auger peak of a standard TiN (Ti+N) material (FIG. 2) overlap, making it difficult to analyze the nitrogen content of the TiN film.

Figure 3:
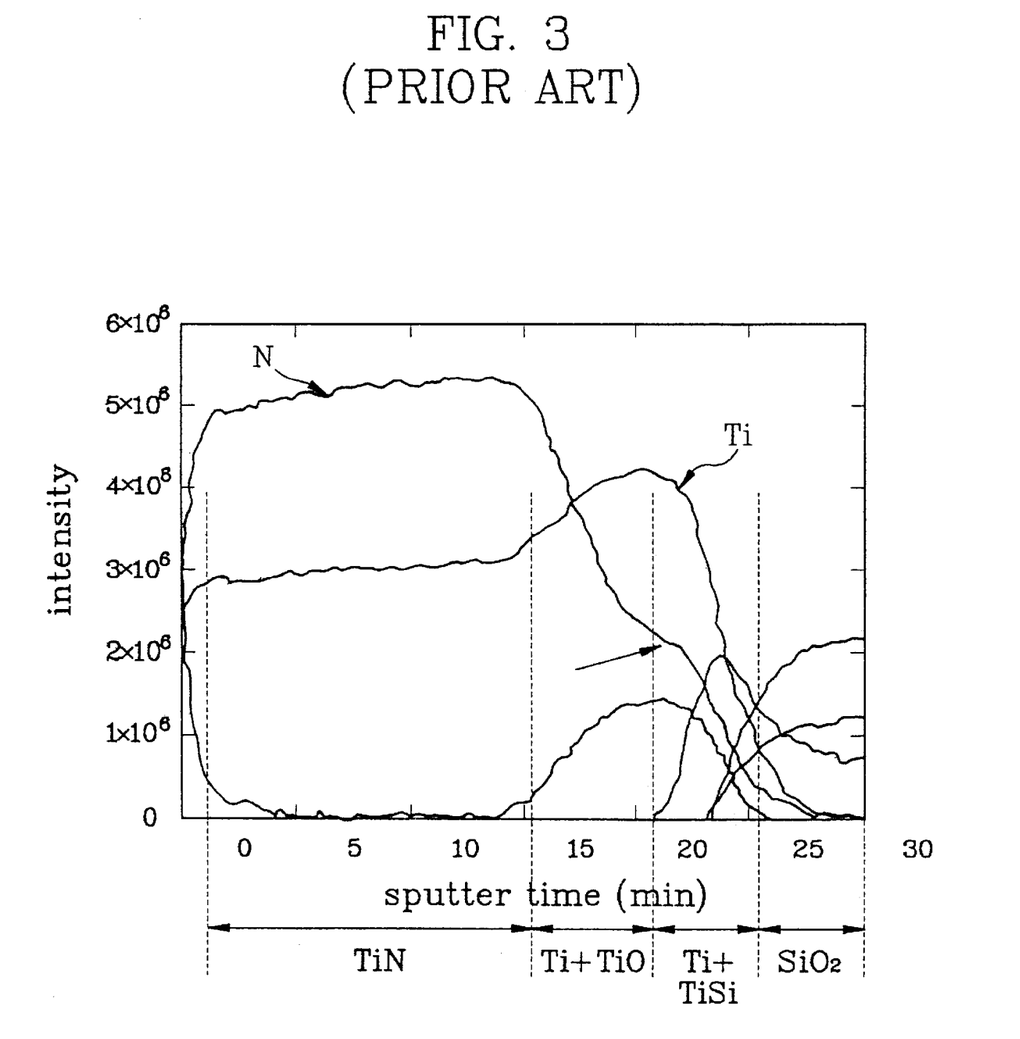
FIG. 3 is a spectrum display showing the correlation between the intensity and the sputter time after analyzing a semiconductor device having TiN/Ti films as a barrier metal layer obtained by conventional AES.
Figure 4:
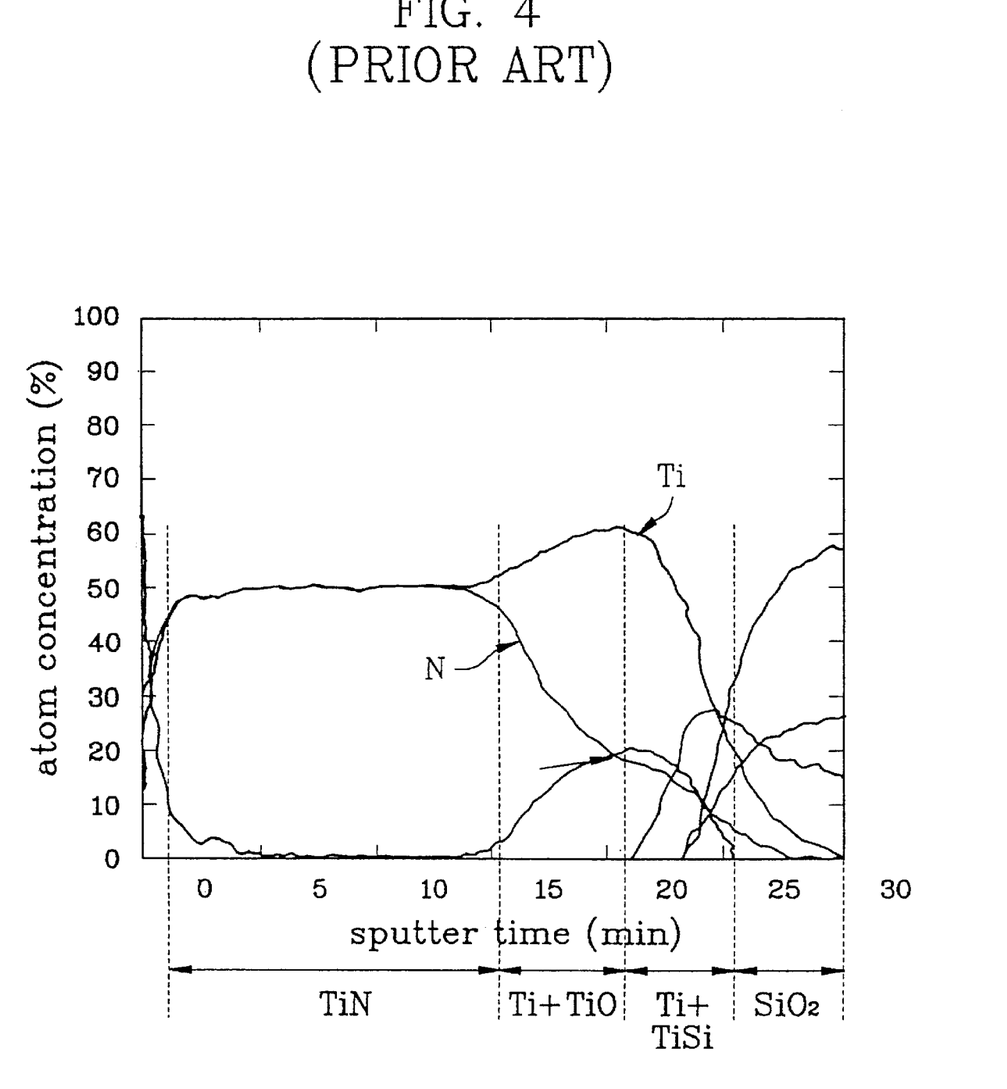
FIG. 4 is a spectrum display showing the correlation between the atom concentration and the sputter time after analyzing a semiconductor device having TiN/Ti films as a barrier metal layer obtained by conventional AES.

FIG. 3 and FIG. 4 depict the spectra of a semiconductor device having TiN/Ti films as a barrier metal film, wherein the intensity and atom concentration are correlated to the sputter time, respectively. Note that the peaks of the N and the Ti overlap so as to make the separation of the N peak difficult, which decreases the reliability in calculating the component ratio. The un-designated arrows in FIGS. 3 and 4 point to a region wherein, although the intensity value of the titanium and nitrogen components appears to overlap, the nitrogen component is not present as shown by the elapsed sputter time for a sample comprising $TiN/Ti/SiO_2$/Si-substrate.

Accordingly, there is a need for an AES analysis technique for accurately determining the quantitative and quantitative analysis of the nitrogen content within a TiN film so as to improve the reliability and production capacity of the semiconductor devices having such TiN films.

SUMMARY OF THE INVENTION

An object of the present invention is to provide a method of setting the base energy level for an Auger Electron Spectroscopy (AES) analysis of a Titanium Nitride (TiN) film.

Another object of the present invention is to provide a method of analyzing semiconductor devices, having TiN films formed thereon, using the method of setting the base energy level for AES.

To achieve these and other advantages and in accordance with the purpose of the present invention as embodied and broadly described, there is provided a method of setting a base energy level for an Auger Electron Spectroscopy (AES) analysis of a titanium nitride (TiN) sample. The method includes: a) conducting a first analysis on the TiN sample using AES, which comprises identifying a TiN kinetic energy main-peak from a TiN sample spectrum; b) conducting a second analysis on a titanium (Ti) sample using AES, which comprises identifying a Ti kinetic energy main-peak from a Ti sample spectrum; c) subtracting the Ti sample spectrum from the TiN sample spectrum to obtain a nitrogen (N) sample spectrum, wherein the nitrogen sample spectrum comprises an N kinetic energy main-peak and a plurality of N kinetic energy sub-peaks; d) selecting one of the plurality of N kinetic energy sub-peaks from the N sample spectrum that do not overlap the Ti kinetic energy main-peak; and e) setting the base energy level for the AES analysis of the TiN sample to the kinetic energy of the selected one of the N kinetic energy sub-peaks.

Preferably, the first analysis and the second analysis are each performed at AES kinetic energy levels in a range of about 360 eV to about is 390 eV and at an AES energy resolution of 0.2 eV/step. The N peak selected as the base energy level preferably has a kinetic energy in a range of about 365 eV to about 369 eV, and more preferably 367 eV.

It is to be understood that both the foregoing general description and the following detailed description are exemplary and explanatory and are intended to provide further explanation of the invention as claimed.

DETAILED DESCRIPTION OF THE PREFERRED EMBODIMENTS

The present invention now will be described with reference to the accompanying drawings in which preferred embodiments of the invention are shown. As used herein, the term main-peak refers to the highest kinetic energy peak value of a given spectrum, and sub-peak refers to the one or more kinetic energy peak values less than the main-peak.

Figure 5:
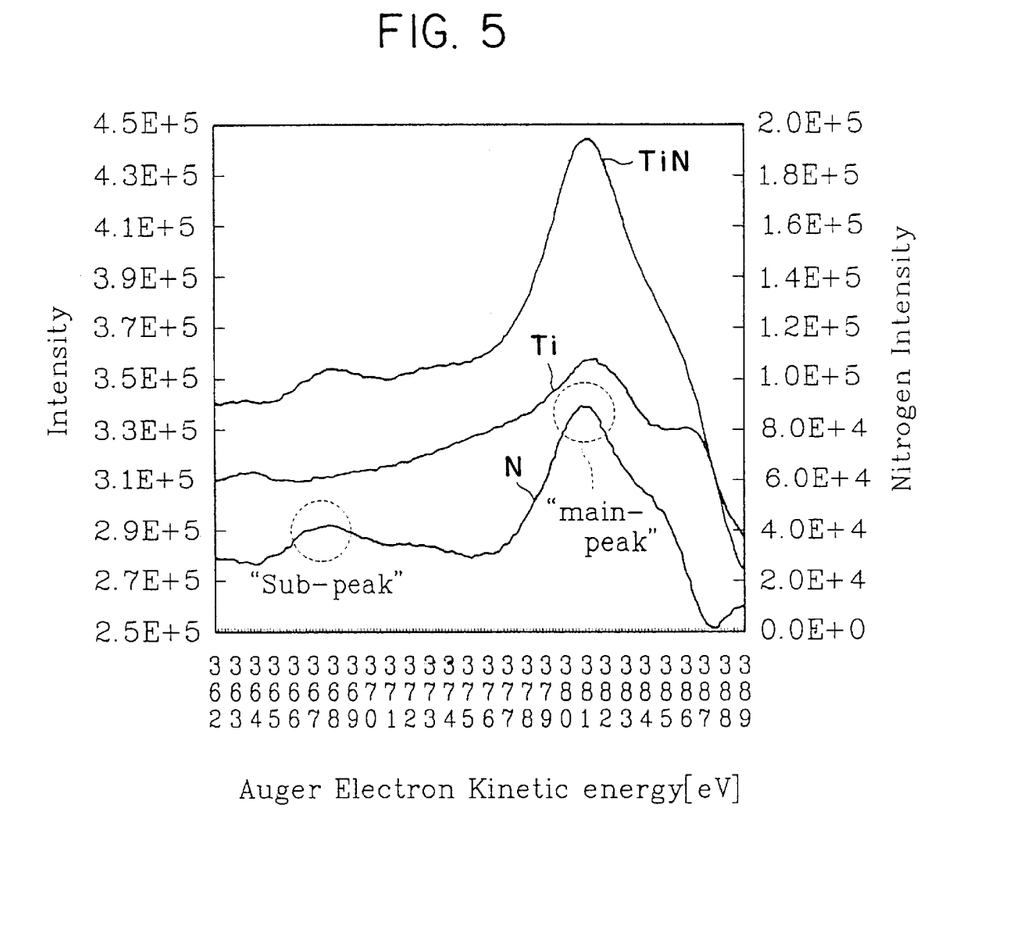
FIG. 5 depicts the TiN, Ti and N spectrum obtained by AES according to the present invention.

As shown in FIG. 5, according to the method of setting the base energy level of Auger Electron Spectroscopy (AES) for a TiN analysis, a TiN kinetic energy main-peak is identified from the AES spectrum of a TiN sample. Next, a titanium (Ti) kinetic energy main-peak is identified from the AES spectrum of a Ti sample. By subtracting the Ti spectrum from the TiN spectrum, one obtains an N-only spectrum having an N kinetic energy main-peak and a plurality of N kinetic energy sub-peaks. Then, one of the plurality of N kinetic energy sub-peaks is selected, which does not overlap the Ti kinetic energy main-peak. Finally, the base energy level for the AES analysis of the TiN sample is set to the kinetic energy of the selected one of the N kinetic energy sub-peaks which does not overlap the Ti kinetic energy main-peak.

In sum, a TiN peak is first confirmed from a TiN standard sample (the first analysis step), a Ti peak is confirmed from a Ti sample (the second analysis step), an N sample is obtain by subtraction of the Ti sample from the TiN sample (subtraction step), one of the plurality of N kinetic energy sub-peaks from the N sample spectrum that do not overlap the Ti kinetic energy main-peak is selected (selection step), and the base energy level for the AES analysis is set to the kinetic energy of the selected one of the N kinetic energy sub-peaks (setting step).

Conventionally, it was difficult to distinguish an N peak and a Ti peak in the TiN spectrum under AES analysis, since the N peak and the Ti peak nearly overlap each other. Thus, in the present invention, a different, non-overlapping N peak is selected by comparison with a Ti peak of a Ti only sample.

According to this method of setting the base energy level for the AES analysis, the kinetic energy range from 360 eV to 390 eV (where normal N peaks are found) is first examined. Preferably, the above described first analysis and the second analysis are carried out at an AES energy resolution of 0.2 eV/step, which increases the resolution of the peaks, and as a result, the confirmation of the peaks and the intensity is easily accomplished.

Each peak of the first analysis and the second analysis is shown as the intensity, or differential value of the intensity, with respect to the AES kinetic energy values, and the height or the maximum point and the minimum point of peaks are clearly seen therefrom. Also, the atom concentration or atom density proportional to the height can be accurately calculated.

As a result of the analysis, it was determined that the kinetic energy of the N sub-peaks which overlap with the Ti peak are in a range from 373 to 383 eV. Therefore, by selecting the highest N sub-peak from among the N sub-peaks that do not overlap with the Ti peak, the N sub-peak is easily confirmed and the kinetic energy of this selected N sub-peak is in a range from 365 eV to 369 eV, and preferably 367 eV.

Figure 6A:
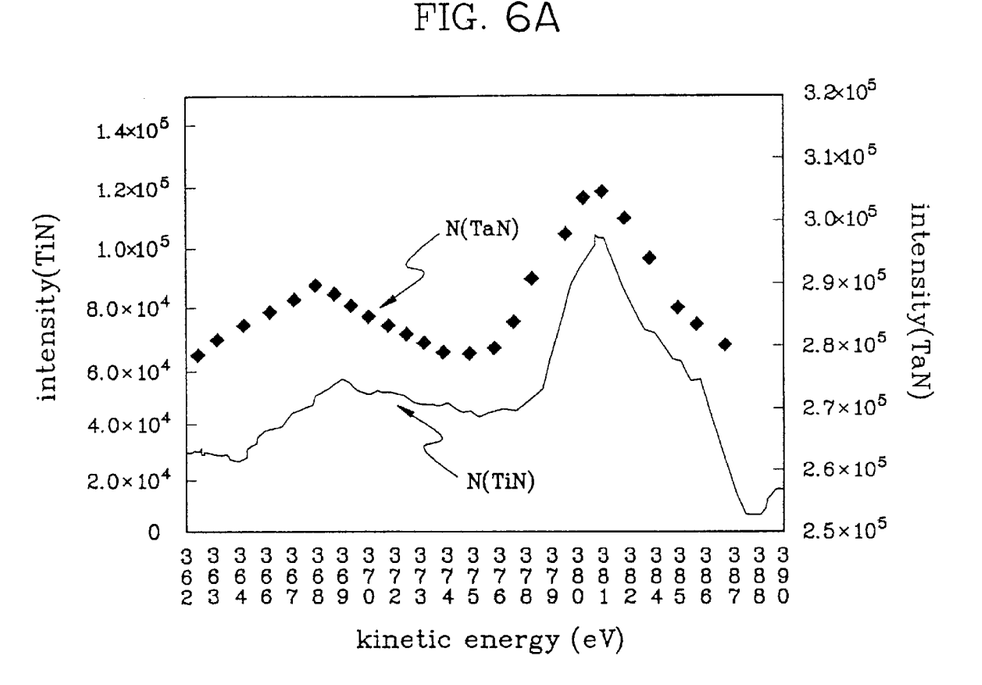
FIG. 6A depicts the TiN and TaN spectrum obtained by AES according to the present invention.

To check whether the selected N sub-peak is a valid N sub-peak or not, a verification step may be performed. The verification step is carried out by identifying the N kinetic energy peak from the peaks of a chemical compound of another different sample, which includes N and another element X but does not include Ti. The N kinetic energy peaks from this different sample (X—N) are compared to the kinetic energy of the selected base energy level to verify that the kinetic energy of the selected base energy level corresponds to an N kinetic energy peak of the different sample. Tantalum Nitride (TaN) is one such different sample, since the tantalum shows similar physical and chemical properties with titanium. As shown in FIG. 6A, and described further later, since the TaN shows similar peaks throughout the range of kinetic energy, it can be used very successfully in the comparison analysis with TiN.

Moreover, according to the present invention, it is possible to analyze a semiconductor device comprising TiN or a device including TiN/Ti as a barrier metal layer. This device analysis is accomplished in the same way, that is, the base energy level of the AES analysis is set to an N kinetic energy sub-peak that does not overlap with the Ti kinetic energy. The analysis for N is thus possible and the N element content is accurately determined by the N kinetic energy sub-peak. As before, the base energy level of the AES analysis is preferably set in a range from 365 eV to 369 eV.

In addition, for multiple-layer semiconductor devices (i.e., comprising TiN/Ti/oxide layer/semiconductor substrate), the above AES analysis may also be applied, whereby the N sub-peak that does not overlap with the Ti peak is selected, and the N atom quantities can be accurately calculated.

Now hereinafter, exemplary embodiments of the present invention are described in detail, but the present invention should not be interpreted as being limited thereto.

Embodiment 1

Referring to FIG. 6A, an AES analysis was carried out for wafers including TiN and TaN (having a similar chemical structure to TiN), using a SAM 4300 apparatus (manufactured by PHI Co. of USA). The ranges of the kinetic energy were from 360 eV to 390 eV. As shown in FIG. 6A, the TiN and TaN peaks show very similar shapes, with both the main-peaks and sub-peaks overlapping.

Figure 6B:
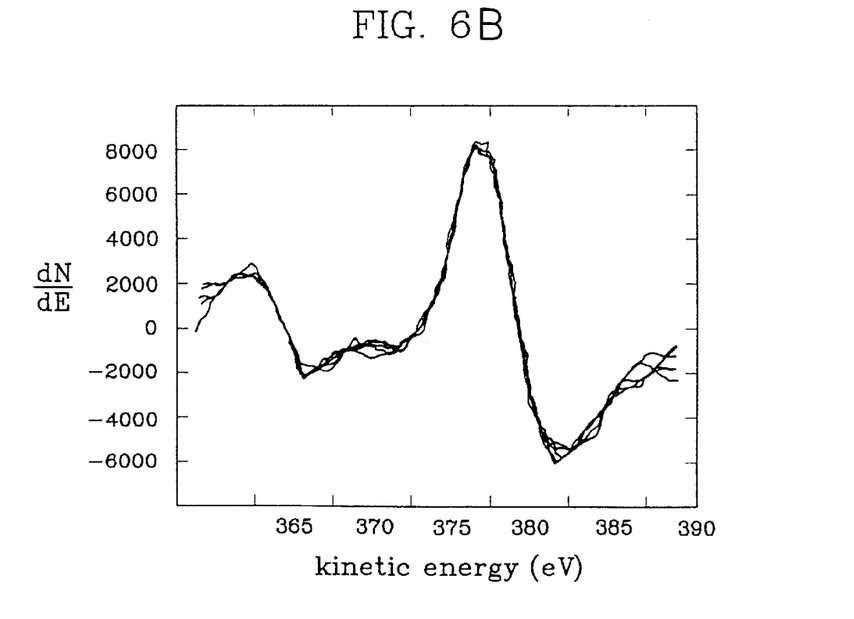
FIG. 6B shows the differential result of the spectrum of the TiN peaks of FIG. 6A.

FIG. 6B depicts the differential value of the main peaks and the sub-peaks of the TiN material among the peaks shown in FIG. 6A. The differential value of the peak height shown in FIG. 6B is proportional to the quantity of N, and the N quantities are readily confirmed from the peak height.

Embodiment 2

Figure 7:
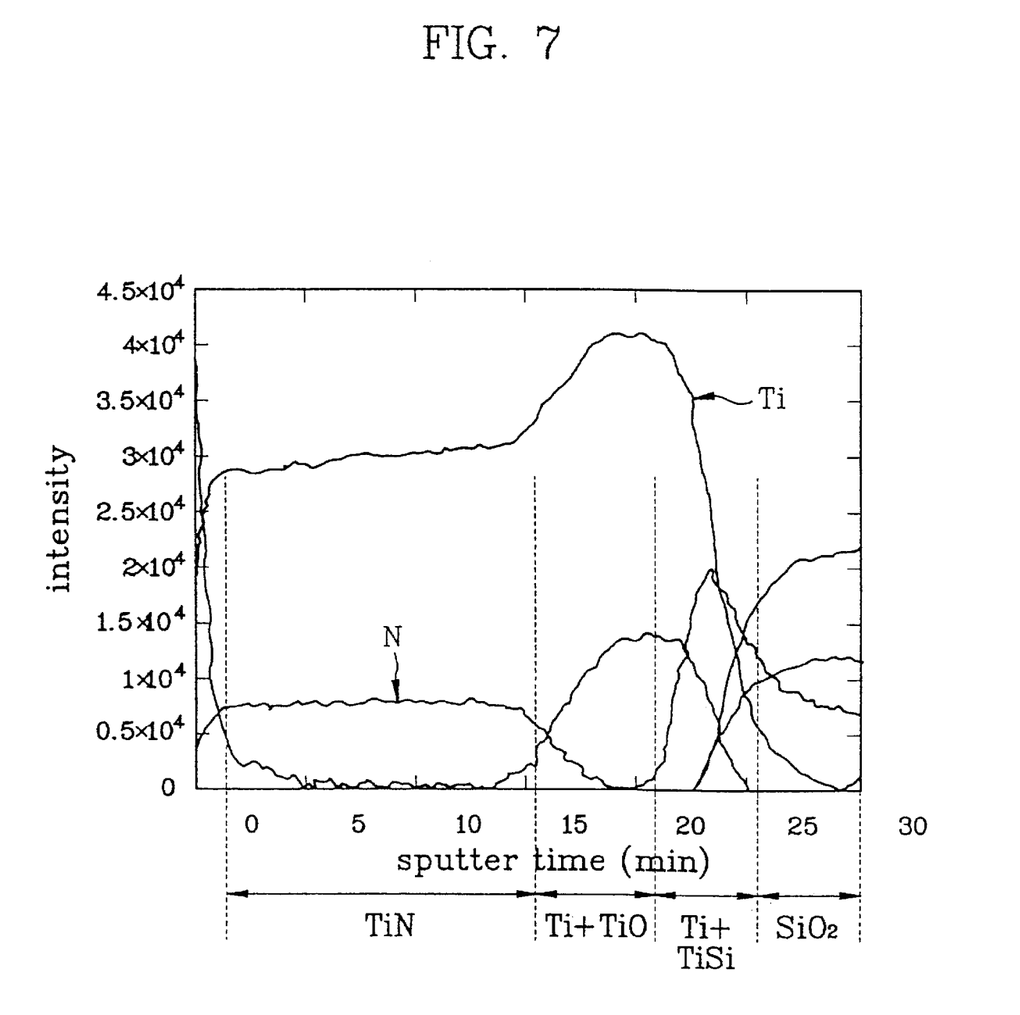
FIG. 7 is a spectrum display showing the correlation between the intensity and the sputter time after analyzing a semiconductor device having TiN/Ti films as a barrier metal layer obtained by AES according to the present invention.

An AES analysis was performed in the same manner as Embodiment 1 for semiconductor devices having barrier layers comprising TiN/Ti, with the N spectrum peak having a kinetic energy ranging from 365 to 370 eV being set as the base energy level of the AES. FIG. 7 is a spectrum display showing the correlation between the intensity and the sputter time of the semiconductor device having a TiN/Ti film as a barrier metal film, and FIG. 8 is a spectrum display showing the correlation between the atom concentration and the sputter time of the semiconductor device having a TiN/Ti film as a barrier metal film.

Figure 8:
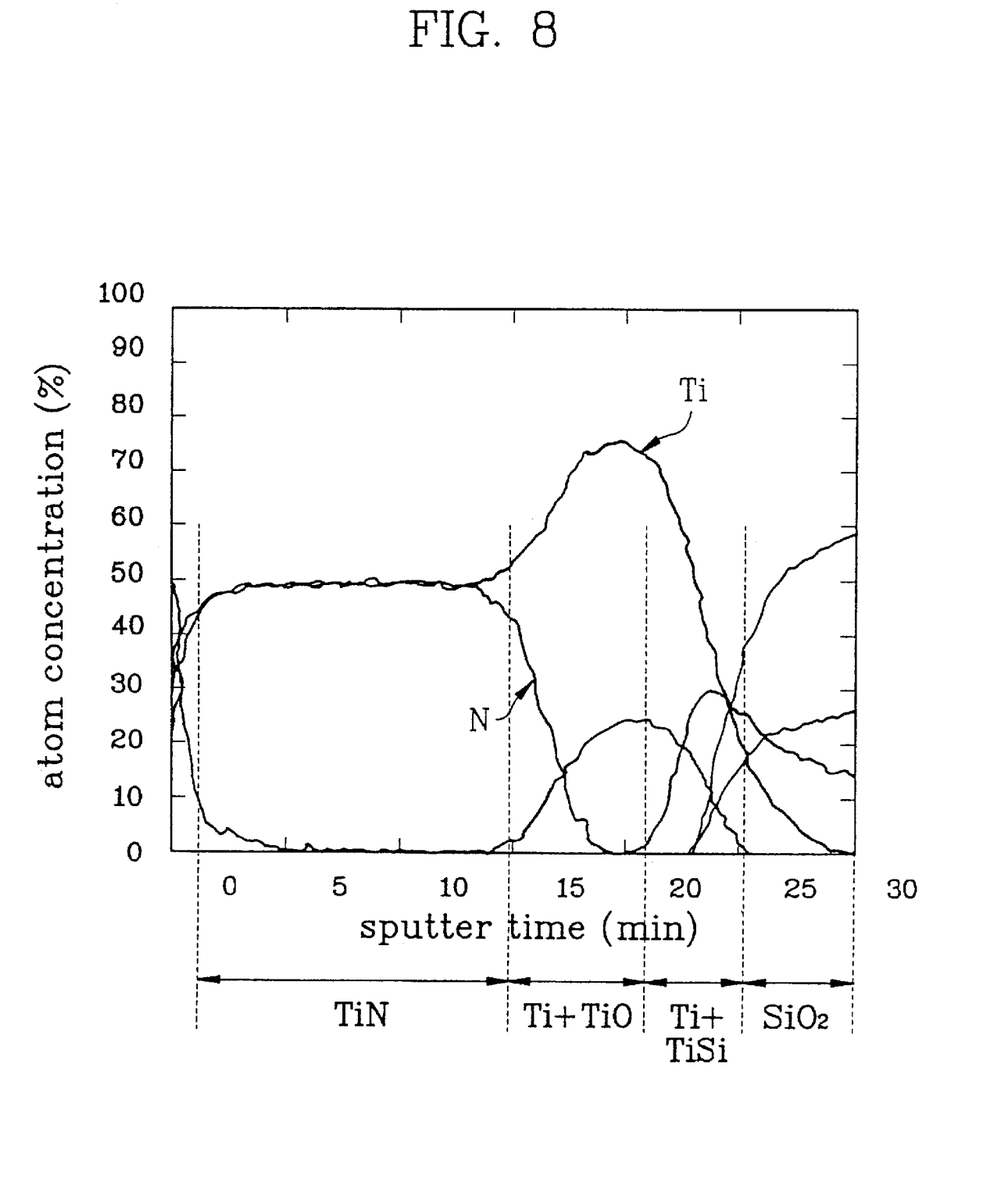
FIG. 8 is a spectrum display showing the correlation between the atom concentration and the sputter time after analyzing a semiconductor device having TiN/Ti films as a barrier metal layer obtained by AES according to the present invention.

In the analysis results shown in FIGS. 7 and 8, an N peak is selected from a kinetic energy range at approximately 368 eV, and is compared with the conventional N peaks selected around 379 eV shown in FIGS. 3 and 4. In FIGS. 7 and 8, the spectrum peaks of each of the elements are clearly separated, and the proportional ratio is accurately calculated therefrom.

Therefore, in accordance with the present invention, it is possible to extract a nitrogen (N) peak which does not overlap with the titanium (Ti) peak. Accordingly, the above analysis results can be used to distinguish the atoms in the specimen by analyzing the obtained spectra corresponding to the atoms. The method of the present invention can also be used to calculate the element component ratio in the sample accurately and with high repeatability. On the other hand, the analysis results obtained by using the conventional AES method (FIGS. 3 and 4), which set the kinetic energy region at around 379 eV, shows the nitrogen peak positioned somewhere within the titanium peaks.

By using the analytical method of the present invention, it is possible to analyze the nitrogen content in a titanium nitride film, to analyze the titanium nitride film itself, and to analyze a semiconductor device having titanium nitride film formed thereon. Also, it is possible to analyze the nitrogen content easily and accurately so as to improve the productivity and quality of a semiconductor device.

Additional advantages and modifications will readily occur to those skilled in the art, and the invention should not be construed as limited to the specific details and representative devices shown and described herein. Accordingly, various modifications may be made without departing from the spirit or scope of the general inventive concept as defined by the appended claims and their equivalents.

What is claimed is:

1. A method of setting a base energy level for an Auger Electron Spectroscopy (AES) analysis of a titanium nitride (TiN) sample, the method comprising:

a) conducting a first analysis on the TiN sample using AES, the first analysis comprising identifying a TiN kinetic energy main-peak from a TiN sample spectrum;

b) conducting a second analysis on a titanium (Ti) sample using AES, the second analysis comprising identifying a Ti kinetic energy main-peak from a Ti sample spectrum;

c) subtracting the Ti sample spectrum from the TiN sample spectrum to obtain a nitrogen (N) sample spectrum, wherein the nitrogen sample spectrum comprises an N kinetic energy main-peak and a plurality of N kinetic energy sub-peaks;

d) selecting one of the plurality of N kinetic energy sub-peaks from the N sample spectrum that do not overlap the Ti kinetic energy main-peak; and e) setting the base energy level for the AES analysis of the TiN sample to the kinetic energy of the selected one of the N kinetic energy sub-peaks.

2. The method of setting the base energy level of claim 1, wherein the first analysis and the second analysis are each performed at an AES kinetic energy in a range of about 360 eV to about 390 eV.

3. The method of setting the base energy level of claim 2, wherein the TiN kinetic energy main-peak and the Ti kinetic energy main-peak overlap at a kinetic energy ranging from about 373 eV to about 383 eV.

4. The method of setting the base energy level of claim 2, wherein the base energy level setting step is carried out by selecting a highest kinetic energy peak of the plurality of N kinetic energy sub-peaks.

5. The method of setting the base energy level of claim 4, wherein the N kinetic energy sub-peak selected as the base energy level has a kinetic energy in a range of about 365 eV to about 369 eV.

6. The method of setting the base energy level of claim 5, wherein the N kinetic energy sub-peak selected as the base energy level has a kinetic energy of 367 eV.

7. The method of setting the base energy level of claim 1, wherein the first analysis and the second analysis are each performed at an AES energy resolution of 0.2 eV/step.

8. The method of setting the base energy level of claim 1, wherein the TiN kinetic energy main-peak of the first analysis and the Ti kinetic energy main-peak of the second analysis are each indicative of an intensity of an AES kinetic energy.

9. The method of setting the base energy level of claim 1, wherein the TiN kinetic energy main-peak of the first analysis and the Ti kinetic energy main-peak of the second analysis are each indicative of a differential value of an AES kinetic energy.

10. The method of setting the base energy level of claim 1, further comprising a verification step, the verification step comprising:

(e) determining second N kinetic energy peaks from a nitride compound X—N containing nitrogen, wherein X represents an element other than titanium;

(f) comparing the kinetic energy of the selected base energy level to the second N kinetic energy peaks; and (g) if the kinetic energy of the selected base energy level equals the kinetic energy of one of the second N kinetic energy peaks, confirming the selected base energy level corresponds to an N kinetic energy sub-peak.

11. The method of setting the base energy level of claim 10, wherein the nitride compound is tantalum nitride (TaN).

12. The method of setting the base energy level of claim 1, wherein the TiN sample comprises a TiN film formed on a semiconductor device.

13. The method of setting the base energy level of claim 1, wherein the TiN sample comprises a barrier metal layer containing TiN film and formed on a semiconductor device.

* * * * *